(12) United States Patent
Takazawa et al.

(10) Patent No.: US 9,790,163 B2
(45) Date of Patent: Oct. 17, 2017

(54) METHOD FOR RECOVERING ANIONIC FLUORINATED EMULSIFIER

(71) Applicant: Asahi Glass Company, Limited, Chiyoda-ku (JP)

(72) Inventors: Masahiro Takazawa, Chiyoda-ku (JP); Shigeru Aida, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 15/263,807

(22) Filed: Sep. 13, 2016

(65) Prior Publication Data

US 2016/0376215 A1    Dec. 29, 2016

Related U.S. Application Data

(63) Continuation of application No. PCT/JP2015/059986, filed on Mar. 30, 2015.

(30) Foreign Application Priority Data

Mar. 31, 2014  (JP) .................................. 2014-072947

(51) Int. Cl.
| | | |
|---|---|---|
| *C07C 53/21* | (2006.01) | |
| *C07C 51/47* | (2006.01) | |
| *B01J 41/05* | (2017.01) | |
| *B01J 41/07* | (2017.01) | |
| *B01J 47/016* | (2017.01) | |

(52) U.S. Cl.
CPC .............. *C07C 51/47* (2013.01); *B01J 41/05* (2017.01); *B01J 41/07* (2017.01); *B01J 47/016* (2017.01)

(58) Field of Classification Search
CPC ......... C07C 51/47; B01J 47/016; B01J 41/05; B01J 41/07

USPC ......................................................... 562/605
See application file for complete search history.

(56) References Cited

U.S. PATENT DOCUMENTS 6,518,442 B1    2/2003  Felix et al.

FOREIGN PATENT DOCUMENTS

| JP | 63-2656 | 1/1988 |
|---|---|---|
| JP | 2002-516885 | 6/2002 |
| JP | 2002516885 A * | 6/2002 |
| JP | 2003-94052 | 4/2003 |
| JP | 2003094052 A * | 4/2003 |
| JP | 2007-98240 | 4/2007 |
| WO | WO 2011/096448 A1 | 8/2011 |
| WO | WO 2014/136692 A1 | 9/2014 |

OTHER PUBLICATIONS

English Translation of International Search Report issued Jun. 23, 2015 in PCT/JP2015/059986, filed Mar. 30, 2015.

\* cited by examiner

*Primary Examiner* — Deborah D Carr
(74) *Attorney, Agent, or Firm* — Oblon, McClelland, Maier & Neustadt, L.L.P.

(57) ABSTRACT

To provide a method for recovering an acid of an anionic fluorinated emulsifier with a high yield from a basic ion exchange resin having a nonionic surfactant physically adsorbed thereon and having the anionic fluorinated emulsifier adsorbed thereon. A method for eluting and recovering an acid of an anionic fluorinated emulsifier from a basic ion exchange resin having a nonionic surfactant physically adsorbed thereon and having the anionic fluorinated emulsifier adsorbed thereon, which comprises a step (1) of bringing the basic ion exchange resin into contact with a water-soluble organic solvent and a step (2) of recovering the acid of the anionic fluorinated emulsifier from the basic ion exchange resin from which the ionic surfactant is eluted in the step (1).

14 Claims, No Drawings

METHOD FOR RECOVERING ANIONIC FLUORINATED EMULSIFIER

TECHNICAL FIELD

The present invention relates to a method for recovering an anionic fluorinated emulsifier as an acid from a basic ion exchange resin having the anionic fluorinated emulsifier adsorbed thereon.

BACKGROUND ART

A fluorinated polymer such as a polytetrafluoroethylene (hereinafter referred to as PTFE), a melt-processable fluororesin or a fluoroelastomer is produced by emulsion polymerization of a fluorinated monomer using an anionic fluorinated emulsifier (hereinafter referred to as AFE).

Since the AFE is not easily decomposed in the natural world, in recent years, it is required to reduce an anionic fluorinated emulsifier contained in industrial effluents and in products such as a fluorinated polymer aqueous dispersion, etc.

Usually, a fluorinated polymer aqueous dispersion (hereinafter referred to as AD) is produced by adding a nonionic surfactant (hereinafter referred to as NSAA) to a fluorinated polymer aqueous emulsion obtained by emulsion polymerization to stabilize the emulsion, followed by concentration. On that occasion, the AD containing the AFE is brought into contact with a basic ion exchange resin (hereinafter referred to as a basic IER) so that the AFE is adsorbed on the basic IER, thereby to reduce the content of the AFE in the AD. Since the AFE is expensive, attempts have been made to recover and recycle the AFE adsorbed on the basic IER.

For example, Patent Document 1 discloses a method of treating a basic IER having an AFE adsorbed thereon, with a mixture of a dilute mineral acid and an organic solvent, to recover the AFE as an acid. It is disclosed that the organic solvent is preferably a solvent which is miscible with water to present a solubility of at least 40% or which can be unlimitedly mixed with water, and an alcohol such as methanol, a cyclic ether such as dioxane, methylene chloride, etc. may be used.

In Examples in Patent Document 1, the AFE was recovered with a high yield of at least 80% from a weakly basic IER using as the organic solvent an alcohol such as methanol or a cyclic ether such dioxane.

In Examples in Patent Document 2, the AFE was recovered with a high yield of at least 80% from a basic IER using an aqueous inorganic acid solution, an organic solvent having a nitrile group and a fluorinated medium. However, it was found that since the basic IER having the AFE adsorbed thereon obtained in the step of reducing the AFE in the AD, has the NSAA physically adsorbed thereon, when the acid of the AFE is separated and purified, the recovery rate of the AFE is lowered by influences of the NSAA and its decomposed products.

PRIOR ART DOCUMENTS

Patent Documents

Patent Document 1: JP-B-S63-2656
Patent Document 2: WO2011/096448

DISCLOSURE OF INVENTION

Technical Problem

It is an object of the present invention to provide a method for recovering an acid of an AFE from a basic IER having a NSAA physically adsorbed thereon and having the AFE adsorbed thereon.

Solution to Problem

The present invention provides a method for recovering an AFE, having the following constructions [1] to [14].

[1] A method for recovering an AFE, which comprises eluting an AFE from a basic IER having a NSAA physically adsorbed thereon and having the AFE adsorbed thereon and recovering it as an acid of the AFE, and which is characterized by comprising a step (1) of bringing the basic IER into contact with a water-soluble organic solvent, and then a step (2) of recovering the acid of the AFE from the basic IER from which the ionic surfactant is eluted in the step (1).

[2] The method for recovering an AFE according to the above [1], wherein the step (2) comprises a step (2-1) of bringing the basic IER into contact with an aqueous inorganic acid solution and a water-soluble organic solvent.

[3] The method for recovering an AFE according to the above [1] or [2], wherein the step (2) comprises the above step (2-1), and a step (2-2) of separating the mixture into the basic IER and a liquid phase and recovering the liquid phase, and a step (2-3) of recovering the acid of the AFE from the liquid phase, in this order.

[4] The method for recovering an AFE according to the above [2] or [3], wherein the step (2-1) comprises a step (2-1-1) of bringing the basic IER into contact with the aqueous inorganic acid solution and then a step (2-1-2) of bringing the basic IER into contact with the water-soluble organic solution.

[5] The method for recovering an AFE according to the above [4], which comprises the above step (2-1-1), then a step (2-1-1-2) of separating and recovering the basic IER, and then the step (2-1-2).

[6] The method for recovering an AFE according to any one of the above [1] to [5], wherein the water-soluble organic solvent is at least one member selected from the group consisting of an organic solvent having a nitrile group, an alcohol, a ketone and an ester.

[7] The method for recovering an AFE according to any one of the above [2] to [6], wherein the aqueous inorganic acid solution is at least one member selected from the group consisting of an aqueous hydrochloric acid solution, an aqueous sulfuric acid solution, an aqueous nitric acid solution and an aqueous phosphoric acid solution.

[8] The method for recovering an AFE according to any one of the above [1] to [7], wherein the water-soluble organic solvent is an organic solvent having a nitrile group, and the organic solvent having a nitrile group is at least one member selected from the group consisting of acetonitrile, propionitrile, butyronitrile and isobutyronitrile.

[9] The method for recovering an AFE according to any one of the above [1] to [8], wherein the acid of the AFE is a fluorinated carboxylic acid.

[10] The method for recovering an AFE according to the above [9], wherein the acid of the AFE is a $C_{5-7}$ fluorinated carboxylic acid which may have from 1 to 3 etheric oxygen atoms.

[11] The method for recovering an AFE according to any one of the above [1] to [10], wherein the basic IER is a strongly basic IER.

[12] The method for recovering an AFE according to any one of the above [2] to [11], wherein the concentration of the aqueous inorganic acid solution is at least 5.0 mass %.

[13] The method for recovering an AFE according to any one of the above [2] to [12], wherein the amount of the inorganic acid in the aqueous inorganic acid solution is within such a range that the acid of the AFE to be eluted/the inorganic acid is from 1/20 to 1.5/1 by the molar ratio.

[14] The method for recovering an AFE according to any one of the above [2] to [13], wherein the ratio of the basic IER to the aqueous inorganic acid solution is from 90/10 to 10/90 by the mass ratio.

[15] The method for recovering an AFE according to any one of the above [2] to [14], wherein the ratio of the basic IER to the water-soluble organic solvent is from 10/90 to 70/30 by the mass ratio.

Advantageous Effects of Invention

The present invention provides a method for efficiently recovering an acid of an AFE from a basic IER having a NSAA physically adsorbed thereon and having the AFE adsorbed thereon. The recovered acid of the AFE can easily be separated and purified.

DESCRIPTION OF EMBODIMENTS

In the present invention, the NSAA contained in the AD is not particularly limited. The NSAA may, for example, be a NSAA represented by the formula (A) or (B):

$$R^1\text{—O-A-H} \tag{A}$$

wherein $R^1$ is a $C_{8-18}$ alkyl group, and A is a polyoxyalkylene chain composed of 5 to 20 oxyethylene groups and 0 to 2 oxypropylene groups:

$$R^2\text{—}C_6H_4\text{—O—B—H} \tag{B}$$

wherein $R^2$ is a $C_{4-12}$ alkyl group, and B is a polyoxyethylene chain composed of 5 to 20 oxyethylene groups.

Specific examples of the NSAA of the formula (A) include, for example, NSAAs having molecular structures of $C_{13}H_{27}$—$(OC_2H_4)_{10}$—OH, $C_{12}H_{25}$—$(OC_2H_4)_{10}$—OH, $C_{10}H_{21}CH(CH_3)CH_2$—$(OC_2H_4)_9$—OH, $C_{13}H_{27}$—$(OC_2H_4)_8$—$OCH(CH_3)CH_2$—OH, $C_{16}H_{33}$—$(OC_2H_4)_{10}$—OH, $CH(C_5H_{11})(C_7H_{15})$—$(OC_2H_4)_9$—OH, etc. Commercial products include TERGITOL (registered trademark) 15S series, manufactured by The Dow Chemical Company, Newcol (registered trademark) series, manufactured by Nippon Nyukazai Co., Ltd., Lionol (registered trademark) TD series, manufactured by Lion Corporation, etc.

Specific examples of the NSAA of the formula (B) include, for example, NSAAs having molecular structures of $C_8H_{17}$—$C_6H_4$—$(OC_2H_4)_{10}$—OH, $C_9H_{19}$—$C_6H_4$—$(OC_2H_4)_{10}$—OH, etc. Commercial products include Triton (registered trademark) X series, manufactured by The Dow Chemical Company, Nikkol (registered trademark) OP series or NP series, manufactured by Nikko Chemicals Co., Ltd., etc.

The content of the NSAA represented by the formula (A) and/or (B) in the AD is preferably from 1 to 20 mass %, more preferably from 1 to 10 mass %, particularly preferably from 2 to 8 mass % based on the mass of the fluorinated polymer.

The NSAA is more preferably the NSAA represented by the formula (A) which is excellent in the environmental compatibility.

Specific examples of the acid of the AFE in the present invention include a perfluorocarboxylic acid, a perfluorocarboxylic acid having an etheric oxygen atom, a fluorinated carboxylic acid having a hydrogen atom, a fluorinated sulfonic acid, etc.

The acid of the AFE is preferably a $C_{5-7}$ fluorinated carboxylic acid which may have from 1 to 3 etheric oxygen atoms. Such a fluorinated carboxylic acid has a low bioaccumulation potential and has less environmental impact.

The perfluorocarboxylic acid includes, for example, perfluorohexanoic acid, perfluoroheptanoic acid, perfluorooctanoic acid, perfluorononanoic acid, etc.

The perfluorocarboxylic acid having an etheric oxygen atom includes, for example, $C_3F_7OCF(CF_3)CF_2OCF(CF_3)$COOH, $C_4F_9OC_2F_4OCF_2$COOH, $C_3F_7OC_2F_4OCF_2$COOH, $C_2F_5OC_2F_4OCF_2$COOH,  $C_2F_5OCF_2CF_2OCF_2CF_2OCF_2$COOH, $C_2F_5O(CF_2)_5$COOH, $CF_3OC_2F_4OCF_2$COOH, $CF_3OCF_2OCF_2OCF_2$COOH, $CF_3OCF_2OCF_2OCF_2OCF_2$COOH, $CF_3O(CF_2CF_2O)_2CF_2$COOH, $CF_3OCF_2CF_2CF_2OCF_2$COOH, $CF_3OCF_2CF_2CF_2OCF_2CF_2$COOH, $C_4F_9OCF_2$COOH, $C_4F_9OCF_2CF_2$COOH, $CF_3OCF(CF_3)CF_2OCF(CF_3)$COOH, $C_4F_9OCF(CF_3)$COOH, $C_3F_7OCF(CF_3)$COOH, etc.

The perfluorocarboxylic acid having an etheric oxygen atom is preferably a $C_{5-7}$ perfluorocarboxylic acid having from 1 to 3 etheric oxygen atoms. Its specific examples include $C_3F_7OC_2F_4OCF_2$COOH, $C_2F_5OC_2F_4OCF_2$COOH, $CF_3OC_2F_4OCF_2$COOH, $CF_3OCF_2OCF_2OCF_2$COOH,  $CF_3OCF_2OCF_2OCF_2OCF_2$COOH, $CF_3O(CF_2CF_2O)_2CF_2$COOH, $CF_3OCF_2CF_2CF_2OCF_2$COOH, $C_4F_9OCF_2$COOH, $C_4F_9OCF_2CF_2$COOH, $CF_3OCF(CF_3)CF_2OCF(CF_3)$COOH, $C_4F_9OCF(CF_3)$COOH, $C_3F_7OCF(CF_3)$COOH, etc.

The fluorinated carboxylic acid having a hydrogen atom includes ω-hydroperfluorooctanoic acid, $C_3F_7OCF(CF_3)CF_2OCHF$COOH, $C_2F_5OCF(CF_3)CF_2OCHF$COOH, $CF_3OCF(CF_3)CF_2OCHFCF_2$COOH, $CF_3O(CF_2)_3OCHFCF_2$COOH, $CF_3O(CF_2)_3OCHF$COOH, $C_3F_7OCHFCF_2$COOH, $CF_3CFHO(CF_2)_3$COOH, etc.

The fluorinated carboxylic acid having a hydrogen atom is preferably a $C_{5-7}$ fluorinated carboxylic acid having a hydrogen atom and having from 1 to 3 etheric oxygen atoms. Its specific examples include $CF_3OCF(CF_3)CF_2OCHFCF_2$COOH, $CF_3O(CF_2)_3OCHFCF_2$COOH, $CF_3O(CF_2)_3OCHF$COOH, $C_3F_7OCHFCF_2$COOH, $CF_3CFHO(CF_2)_3$COOH, etc.

The fluorinated sulfonic acid includes perfluorooctanesulfonic acid, $C_6F_{13}CH_2CH_2SO_3H$, etc.

The AFE includes the above acid of the AFE, and its ammonium salt and alkali metal salt. The alkali metal include Li, Na, K, etc. The AFE is preferably an ammonium salt of the above acid.

In the present invention, the basic IER used to adsorb the AFE is not particularly limited and includes a strongly basic ion exchange resin (hereinafter referred to as a strongly basic IER) and a weakly basic ion exchange resin (hereinafter referred to as a weakly basic IER).

The strongly basic IER may be one having a quaternary ammonium group such as a trimethylammonium group or a dimethylethanolammonium group introduced as an ion exchange group to a resin matrix.

The weakly basic IER may be one having a primary to tertiary amino group such as a dimethylammonium group or an amino group introduced as an ion exchange group to a resin matrix.

The material for the resin matrix of the basic IER is not particularly limited. A styrene/divinyl benzene cross-linked resin, an acryl/divinyl benzene cross-linked resin or a cellulose resin may, for example, be mentioned.

The type of the basic IER is not particularly limited, and either porous type or gel type may be preferably used. Particularly, with the porous type, which has a large specific surface area and on which the NSAA is physically adsorbed in a large amount, adsorption and removal are conducted efficiently.

The average particle size of the basic IER is preferably from 0.1 to 5 mm, more preferably from 0.2 to 2 mm, particularly preferably from 0.3 to 1.5 mm. When the average particle size of the basic IER is within the above range, for example, the flow path of the AD is less likely to be clogged, when the AD containing the AFE is permitted to flow through a column packed with the basic IER to carry out the operation to let the AFE be adsorbed.

The ion exchange capacity of the basic IER is preferably from 0.1 to 3 (eq/L), more preferably from 0.5 to 2.5 (eq/L). When the ion exchange capacity of the basic IER is within the above range, the AFE in the AD can efficiently be adsorbed.

Commercial products of the basic IER include, for example, Lewatit (registered trademark) MP800OH, Lewatit (registered trademark) M800KR, Lewatit (registered trademark) MP600 and Lewatit (registered trademark) MP62WS manufactured by Lanxess, PUROLITE (registered trademark) A200MBOH and PUROLITE (registered trademark) A300MBOH manufactured by Purolite K.K., PUROLITE (registered trademark) A503OH manufactured by Purolite K.K., DIAION (registered tradename) manufactured by Mitsubishi Chemical Corporation, AMBERLITE (registered trademark) manufactured by The Dow Chemical Company.

In the present invention, the basic IER having a NSAA physically adsorbed thereon and having an AFE adsorbed thereon, is obtainable by bringing an AD containing a NSAA and an AFE into contact with a basic IER. That is, by bringing the AD into contact with a basic IER, the AFE in the AD is adsorbed on the basic IER, and part of the NSAA is physically adsorbed. For example, in a case where an AD containing $CF_3CF_2OCF_2CF_2OCF_2COONH_4$ as an AFE is brought into contact with a basic IER, $CF_3CF_2OCF_2CF_2OCF_2COO^-$ is considered to be bonded to and adsorbed on an ion exchange group of the basic IER. On that occasion, part of the NSAA in the AD is physically adsorbed on the basic IER. Most part of the NSAA remains in the AD to stably disperse the fluorinated polymer. However, the NSAA physically adsorbed influences the subsequent steps for eluting and recovering the AFE and lowers the recovery rate of the AFE.

As the AD containing a NSAA and an AFE, an AD obtained by subjecting a fluorinated monomer to emulsion polymerization in the presence of an AFE, and adding a NSAA to the obtained fluorinated polymer aqueous emulsion for stabilization, if required, followed by concentration, may be mentioned.

The method for bringing the AD containing a NSAA and an AFE and the basic IER into contact with each other is not particularly limited, and a conventional method may be mentioned. For example, it may be a method of putting the basic IER into the AD, followed by stirring or vibrating, or a method of passing the AD through a column packed with the basic IER. Further, as a step prior to bringing the AD into contact with the basic IER, the AD may preferably be subjected to filtration to remove any floating solid, etc. such as coagulation, whereby it is possible to prevent e.g. clogging of the basic IER. Such filtration of the fluorinated polymer aqueous dispersion is preferably conducted by means of a single stage or multistage filters having pore sizes of from 0.1 to 300 μm, preferably from 1 to 100 μm.

The contact temperature at the time of brining the AD containing a NSAA and an AFE into contact with the basic IER is not particularly limited. It may suitably be selected but is preferably in the vicinity of room temperature of from 10 to 40° C., more preferably from 15 to 35° C. Further, the contact time is not particularly limited and may suitably be selected. For example, in the case of contact by a stirring system, it is preferably within a range of from 10 minutes to 200 hours, more preferably within a range of from 30 minutes to 50 hours. Further, the pressure at the time of contact is preferably the atmospheric pressure, but it may be under a reduced pressure condition or an elevated pressure condition.

As mentioned above, by letting the AFE in the AD be adsorbed on the basic IER, followed by separating the basic IER, it is possible to obtain the basic IER having the NSAA physically adsorbed thereon and having the AFE adsorbed thereon. Such a basic IER having the AFE adsorbed thereon may be used in a wet state without conducting drying treatment, etc. or may be subjected to drying treatment and used in a dried state. Industrially, it is preferred to use it as it is in a wet state, whereby the process can be simplified.

As an embodiment of the method for recovering an AFE in the present invention, a step (1) of bringing the basic IER into contact with a water-soluble organic solvent and then a step (2) of recovering the acid of the AFE from the basic IER are carried out.

In the step (1), by bringing the basic IER having the AFE adsorbed thereon into contact with a water-soluble organic solvent, the NSAA physically adsorbed on the basic IER is eluted and extracted in the water-soluble organic solvent. Then, the acid of the AFE is recovered from the basic IER, whereby the AFE can be easily purified and separated, and it can be used as it is or as an ammonium salt, an alkali metal salt or the like after neutralized.

The ratio of the basic IER to the water-soluble organic solvent is such that the basic IER/the water-soluble organic solvent is preferably from 1/99 to 99/1, more preferably from 10/90 to 90/10, further preferably from 10/90 to 70/30, most preferably from 15/85 to 50/50, by the mass ratio. Further, in order that the water-soluble organic solvent is noncombustible, a fluorinated solvent may be added within the above range. The ratio of the fluorinated solvent to the water-soluble organic solvent is such that the fluorinated solvent/the water-soluble organic solvent is preferably from 75/25 to 95/5, more preferably from 80/20 to 90/10 by the mass ratio. Within such a range, the extraction solvent tends to be noncombustible and is excellent in handling efficiency. When the ratio of the basic IER to the water-soluble organic solvent is within the above range, it is possible to efficiently bring the basic IER and the water-soluble organic solvent into contact with each other.

The contact time of the basic IER and the water-soluble organic solvent is preferably from 5 to 500 minutes, more preferably from 10 to 300 minutes. When the contact time is at least 5 minutes, it is possible to sufficiently elute the NSAA. Even if the contact time exceeds 500 minutes, there is no substantial change in the amount of elution of the NSAA, and therefore, the upper limit is preferably 500 minutes.

The temperature at the time of contact of the water-soluble organic solvent is preferably from 5 to 100° C., more preferably from 10 to 80° C. When it is at least 5° C., it is possible to efficiently elute the NSAA. When it is at most 100° C., the water-soluble organic solvent and the acid of the AFE will not be decomposed, and therefore, the upper limit is preferably 100° C.

The method for bringing the basic IER and the water-soluble organic solvent into contact with each other is not particularly limited. For example, a method of putting the basic IER and the water-soluble organic solvent in an autoclave, followed by mechanical stirring by stirring vanes, or a method of bringing the basic IER and the water-soluble organic solvent into contact with each other by means of a shaking machine, may be mentioned. Otherwise, the basic IER may be packed in a column, and the water-soluble organic solvent is permitted to flow therethrough, so that the NSAA may be eluted into the water-soluble organic solvent by a flow-through extraction method.

The water-soluble organic solvent is preferably at least one member selected from the group consisting of an organic solvent having a nitrile group, an alcohol, a ketone and an ester.

The organic solvent having a nitrile group may, for example, be acetonitrile, propionitrile, butyronitrile, isobutyronitrile or benzonitrile. Among them, preferred is at least one member selected from the group consisting of acetonitrile, propionitrile, butyronitrile and isobutyronitrile. Further, since the basic IER contains water, acetonitrile or propionitrile having high compatibility with water is more preferred, and acetonitrile is most preferred.

When the organic solvent having a nitrile group is water-soluble, the penetrability of the organic solvent having a nitrile group to the basic IER will be better, whereby it becomes easy to elute the NSAA from the basic IER.

The alcohol may, for example, be methanol, ethanol, isopropanol or 1-propanol.

The ketone may, for example, be acetone, methyl ethyl ketone or diethyl ketone.

The ester may, for example, be methyl acetate or ethyl acetate.

The water-soluble organic solvent is preferably an organic solvent having a nitrile group, which is the same as the organic solvent preferably used also in the subsequent step of eluting the acid of the AFE from the basic IER.

The solubility of the water-soluble organic solvent in water at 20° C. is preferably at least 5%, more preferably at least 10%, most preferably at least 50%.

By carrying out e.g. a distillation operation of the recovered liquid phase, the NSAA can be removed and the water-soluble organic solvent can be regenerated. Accordingly, the water-soluble organic solvent is preferably readily separated from the NSAA by distillation. If the water-soluble organic solvent forms an azeotropic mixture with the NSAA, it is difficult to regenerate the water-soluble organic solvent.

In the present invention, the method for recovering the AFE from the basic IER having the AFE adsorbed thereon obtained in the step (1) is not particularly limited, and a conventional method may be mentioned.

In the embodiment of the present invention, the step (2) preferably comprises a step (2-1) of bringing the basic IER into contact with an aqueous inorganic acid solution and a water-soluble organic solvent.

Further, the step (2) more preferably comprises the above step (2-1), a step (2-2) of separating the mixture into the basic IER and a liquid phase and recovering the liquid phase, and a step (2-3) of recovering the acid of the AFE from the liquid phase.

Further, the step (2-1) preferably comprises a step (2-1-1) of bringing the basic IER into contact with the aqueous inorganic acid solution and a step (2-1-2) of bringing the basic IER into contact with the water-soluble organic solvent.

It is more preferred that after the step (2-1-1), a step (2-1-1-2) of separating and recovering the basic IER is conducted, and then the step (2-1-2) is conducted.

In the step (2-1-1) of bringing the basic IER into contact with an aqueous inorganic acid solution, the temperature is from 5 to 100° C., preferably from 10 to 80° C., and the contact time is from 5 to 120 minutes, more preferably from 10 to 90 minutes.

In the step (2-1), when the basic IER having the AFE adsorbed thereon is brought into contact with an aqueous inorganic acid solution, the AFE is formed into an acid form by the inorganic acid and is readily eluted from the basic IER. Since the AFE has favorable compatibility with the water-soluble organic solvent, the AFE adsorbed on the basic IER is eluted as an acid of the AFE and is extracted in the water-soluble organic solvent. Particularly, since the organic solvent having a nitrile group as the water-soluble organic solvent does not react with the acid of the AFE like an alcohol, the acid of the AFE extracted, after separated from the organic solvent having a nitrile group, may be used as it is or as an ammonium salt, an alkali metal salt or the like after neutralized.

The elution operation in the steps (2-1-1), (2-1-1-2) and (2-1-2) is preferably carried out stepwise. By the elution operation, first, in the step (2-1-1), the acid of the AFE is not dissolved in the aqueous inorganic acid solution but is a state attached to the basic IER. Then, in the step (2-1-1-2), the basic IER having the acid of the AFE attached thereto is separated, and then in the step (2-1-2), the acid of the AFE is readily dissolved in the water-soluble organic solvent, and the acid of the AFE can be recovered with a high yield.

The aqueous inorganic acid solution of the present invention is preferably at least one member selected from the group consisting of an aqueous hydrochloric acid solution, an aqueous sulfuric acid solution, an aqueous nitric acid solution and an aqueous phosphoric acid solution. In view of the handling efficiency and industrial applicability, more preferred is an aqueous hydrochloric acid solution or an aqueous sulfuric acid solution, and most preferred is an aqueous hydrochloric acid solution.

The concentration of the aqueous inorganic acid solution is preferably at least 5.0 mass %, more preferably at least 8.0 mass %, most preferably at least 10.0 mass %. Further, it is preferably at most 50 mass %, more preferably at most 40 mass %, most preferably at most 38 mass %. Within such a range, the acid of the AFE will be sufficiently ion-exchanged with the IER and will be excellently extracted in the water-soluble organic solvent.

The ratio of the basic ion exchange resin to the aqueous inorganic acid solution is preferably from 90/10 to 10/90, more preferably from 85/15 to 15/85, most preferably from 80/20 to 20/80 by the mass ratio. Within such a range, the basic ion exchange resin and the aqueous inorganic acid solution can be efficiently brought into contact with each other, and an excellent extraction efficiency of the AFE will be achieved.

The amount of the inorganic acid in the aqueous inorganic acid solution to be used is such that the acid of the anionic fluorinated emulsifier to be eluted/the inorganic acid is preferably from 1/20 to 1.5/1, more preferably from 1/18 to 1.7/1, most preferably from 1/15 to 2/1 by the molar ratio. Within such a range, the acid of the AFE can be sufficiently ion-exchanged with the IER, and the acid of the AFE will be excellently eluted.

EXAMPLES

Now, the present invention will be described in further detail with reference to Examples and Comparative Examples. However, it should be understood that the present invention is by no means restricted thereto. Ex. 1 to 10 and 13 are Examples of the present invention, and Ex. 11, 12 and 14 are Comparative Examples. The NSAA removal rate was calculated by the following method.

[Measurement of NSAA Removal Rate (%) and AFE Recovery Rate (%)]

The NSAA was eluted from the basic IER having the NSAA physically adsorbed thereon into acetonitrile, and the content (g) of the NSAA in acetonitrile was measured.

Then, the acid of the AFE was eluted from the basic IER, and the content (g) of the NSAA in the obtained liquid phase having the acid of the AFE recovered therein was measured.

The NSAA content in each liquid phase was determined by quantitative analysis by $^1$H-NMR and $^{19}$F-NMR using a nuclear magnetic resonator JNM-ECP400 manufactured by JEOL Ltd. The NSAA removal rate and the AFE recovery rate were calculated based on the following formula.

NSAA removal rate (%)=[NSAA content (g) in acetonitrile/(NSAA content (g) in acetonitrile+ NSAA content (g) in liquid phase having acid of AFE recovered therein]×100

The AFE recovery rate (%) was calculated in accordance with the following formula by obtaining the amount of the AFE by quantitative analysis by $^{19}$F-NMR.

AFE recovery rate (%)=[AFE (g) in liquid phase having acid of AFE recovered therein/amount (g) of AFE adsorbed on basic IER]×100   [Ex. 1]

2,370 g of water containing 60 g of a NSAA (Newcol 1308-FA(90), nonionic surfactant manufactured by Nippon Nyukazai Co., Ltd.) and 70 g of AFE ($CF_3CF_2OCF_2CF_2OCF_2COONH_4$) and 100 g of a basic IER (Lewatit MonoPlus MP62WS, weakly basic IER manufactured by Lanxess, average particle size: 470 μm, ion exchange capacity: 1.7 meq/ml) were stirred at 25° C. for 8 hours to obtain 156 g of a basic IER having 2.5 mass % of the NSAA and 24 mass % of the AFE adsorbed thereon.

Here, the amount of the NASS adsorbed on the basic IER was obtained from the concentration in the residue. Into a glass bottle, 5 mL of a cobalt thiocycanate solution (obtained by dissolving 87 g of thiocyanic acid and 14 g of cobalt sulfate in about 500 mL of water) and 5 mL of chloroform were put, and further from 1 to 10 mL of a measurement sample was added, followed by vigorous stirring, the mixture was left at rest, and the lower chloroform phase was collected. The absorbance of the collected chloroform phase was measured at 630 nm by a spectrophotometer. Depending upon the amount of the NASS, the chloroform phase turns blue. A calibration curve was prepared by measuring the absorbance in the same method using an aqueous NASS solution having a known concentration, and using the calibration curve, the concentration was obtained.

The AFE amount was obtained from the concentration in the residue. In a glass bottle, 4 mL of a methylene blue solution (obtained by gradually adding 12 g of sulfuric acid to about 500 mL of water, followed by cooling, dissolving 0.03 g of methylene blue and 50 g of anhydrous sodium sulfate, and adding water to adjust the amount to 1 L) and 5 mL of chloroform were put, and further 0.1 g of a measurement sample diluted 1,000 to 3,000-hold was added, followed by vigorous stirring, the mixture was left at rest, and the lower chloroform phase was collected. The collected chloroform phase was subjected to filtration through a filter having pore sizes of 0.2 μm, and the absorbance at 630 nm was measured by a spectrophotometer. Depending upon the amount of the anionic fluorinated emulsifier, the chloroform phase turns blue. A calibration curve was prepared by measuring the absorbance in the same method using 0.1 g of an anionic fluorinated emulsifier solution having a known concentration, and using the calibration curve, the concentration of the anionic fluorinated emulsifier in the measurement sample was determined.

Then, in a beaker having an internal capacity of 50 ml with a cover, 4 g of the basic IER having the AFE adsorbed thereon, 4 g of acetonitrile and 16 g of 1,3-dichloro-1,1,2,2,3-pentafluoropropane (hereinafter referred to as R-225) were charged, and the content was stirred by a magnetic stirrer for 60 minutes while the temperature was kept at 50° C. in a constant temperature bath, followed by cooling to room temperature. Then, the basic IER was separated and removed to obtain a liquid phase containing the NSAA (hereinafter referred to as a NSAA eluate). Then, in a beaker having an internal capacity of 50 ml with a cover, the separated basic IER and 4 g of a 17.5 mass % aqueous hydrochloric acid solution were charged, and the content was stirred by a magnetic stirrer for 60 minutes while room temperature at about 20° C. was maintained. Then, only the aqueous hydrochloric acid solution was withdrawn from the beaker. Then, in the beaker in which the basic IER treated with the aqueous hydrochloric acid solution was contained, 2 g of acetonitrile and 8 g of R-225 were charged, and the content was stirred by a magnetic stirrer for 60 minutes while the temperature was kept at 50° C. in a constant temperature bath, to extract the acid of the AFE. After completion of stirring, the basic IER was separated and removed to obtain a liquid phase (hereinafter referred to as an AFE eluate).

Both the NSAA eluate and the AFE eluate were separated into two phases after left at rest, and only the lower layers were recovered and respectively taken as a NSAA eluate 1 and an AFE eluate 1.

The NSAA contents in the NSAA eluate 1 and the AFE eluate 1 were determined and as a result, the NSAA eluate 1 contained 88 mg of the NSAA and the AFE eluate 1 contained 8 mg of the NSAA. From the results, the NSAA removal rate was calculated to be 92% in accordance with the above formula.

The AFE eluate 1 contained 0.89 g of the acid of the AFE, and the AFE recovery rate was 93%.

[Ex. 2 to 9]

A NSAA eluate 1 and an AFE eluate 1 were obtained in the same manner as in Ex. 1 except that the amounts of the basic IER having the AFE adsorbed thereon obtained in Ex. 1, acetonitrile and R-225 were changed as identified in Table 1. The NSAA contents were measured, and the NSAA removal rate was calculated. The results are shown in Table 1 together with the AFE recovery rate.

[Ex. 10]

In a beaker having an internal capacity of 50 ml with a cover, 4 g of the basic IER having the AFE adsorbed thereon obtained in Ex. 1, 1.5 g of acetonitrile and 6 g of R-225 were charged, and the content was stirred by a magnetic stirred for 60 minutes while the temperature was kept at 40° C. in a constant temperature bath, followed by cooling to room temperature. Then, the basic IER was separated and removed to obtain a liquid phase containing the NSAA (hereinafter referred to as a NSAA eluate). Such an operation was repeated twice. Further, a NSAA eluate 1 and an AFE eluate 1 were obtained in the same manner as in Ex. 1 except that the amounts of acetonitrile and R-225 were changed as identified in Table 1. The NSAA contents were measured, and the NSAA removal rate was calculated in accordance with the above formula. The results are shown in Table 1 together with the AFE recovery rate.

[Ex. 11]

A NSAA eluate 1 and an AFE eluate 1 were obtained in the same manner as in Ex. 7 except that the NSAA eluate 1 was obtained without using acetonitrile. The NSAA contents were measured, and the NSAA removal rate was calculated in the same manner as in Ex. 1. The results are shown in Table 1 together with the AFE recovery rate.

[Ex. 12]

A NSAA eluate 1 and an AFE eluate 1 were obtained in the same manner as in Ex. 7 except that the NSAA eluate 1 was obtained by using a 2 mass % aqueous salt solution instead of acetonitrile. The NSAA contents were measured, and the NSAA removal rate was calculated in the same manner as in Ex. 1. The results are shown in Table 1 together with the AFE recovery rate.

TABLE 1

| Ex. | | 1 | 2 | 3 | 4 | 5 | 6 | 7 | 8 | 9 | 10 | 11 | 12 |
|---|---|---|---|---|---|---|---|---|---|---|---|---|---|
| Amount of basic IER (g) | | 4 | 4 | 4 | 4 | 4 | 4 | 4 | 4 | 4 | 4 | 4 | 4 |
| NSAA eluate | Amount of acetonitrile (g) | 4 | 3 | 2.7 | 2 | 3 | 3 | 16 | 8 | 16 | 1.5 | — | — |
| | Amount of salt solution (g) | — | — | — | — | — | — | — | — | — | — | — | 4 |
| | Amount of R-225 (g) | 16 | 12 | 10.8 | 8 | 12 | 12 | 16 | 16 | 0 | 6 | 16 | 16 |
| AFE eluate | Amount of 17.5% aqueous hydrochloric acid solution (g) | 4 | 4 | 4 | 4 | 4 | 4 | 4 | 4 | 4 | 4 | 4 | 4 |
| | Amount of acetonitrile (g) | 2 | 2 | 2 | 2 | 3 | 1.5 | 3 | 3 | 3 | 2 | 3 | 3 |
| | Amount of R-225 (g) | 8 | 8 | 8 | 8 | 12 | 6 | 12 | 12 | 12 | 8 | 12 | 12 |
| | NSAA in NSAA eluate 1 (mg) | 88 | 88 | 86 | 84 | 88 | 95 | 87 | 93 | 89 | 90 | 81 | 82 |
| | NSAA in AFE eluate 1 (mg) | 8 | 8 | 14 | 13 | 6 | 8 | 3 | 4 | 6 | 2 | 16 | 16 |
| | NSAA removal rate (%) | 92 | 92 | 86 | 87 | 93 | 92 | 96 | 95 | 93 | 98 | 84 | 84 |
| | AFE recovery rate (%) | 93 | 93 | 91 | 92 | 90 | 84 | 88 | 91 | 91 | 96 | 89 | 90 |

It was confirmed that the AFE recovery rate decreased if the NSAA was contained in the post-step of recovering the acid of the AFE from the basic IER having the AFE adsorbed thereon into the AFE eluate 1 and then recovering the acid of the AFE by separation and purification from the AFE eluate 1 by distillation.

That is, in Examples of the present invention (Ex. 1 to 10), the NSAA recovery rate was high as compared with Comparative Examples (Ex. 11 and 12) in which no water-soluble organic solvent was used. Particularly in Examples of the present invention, the NSAA content in the AFE eluate 1 was low, and the recovery of the acid of the AFE in the post-step was not impaired, and thus the recovery rate of the acid of the AFE was high.

When the NSAA recovery rate is at least 85%, when the acid of the AFE was separated and purified by distillation, the recovery rate of the acid of the AFE contained in the AFE eluate 1 is 90% or higher while the amount of impurities is suppressed to 0.2% or lower. Whereas when the NSAA removal rate is lower than 85% as in Comparative Examples, it is not possible to satisfy both an amount of impurities of 0.2% or lower and a recovery rate of the acid of the AFE contained in the AFE eluate 1 of 90% or higher. In fact, in Comparative Examples, the recovery rate of the acid of the AFE was so low as 70% even though the AFE recovery rate was somewhat high.

[Ex. 13]

The acid of the AFE recovered in Ex. 5 was purified by distillation, whereupon the acid of the AFE with a purity of at least 99.8% was obtained with a yield of 90%. Accordingly, the recovery rate of the acid of the AFE with a purity of 99.8% from the IER was 81%.

[Ex. 14]

The acid of the AFE was purified by distillation in the same manner as in Ex. 13 except that the acid of the AFE used for distillation was changed to the acid of the AFE obtained in Ex. 12. As a result, the yield of the acid of the AFE with a purity of at least 99.8% was 70%, and the recovery rate of the acid of the AFE with a purity of at least 99.8% from the IER was 63%.

As described above, in a case where the acid of the AFE was distilled in a state where removal of the NSAA is insufficient, impurities resulting from decomposition of the NSAA are hardly separated by distillation, and a high purity AFE can hardly be obtained by distillation.

INDUSTRIAL APPLICABILITY

The method for recovering an AFE of the present invention, by which an AFE can be recovered with a high yield from a basic IER having a NSAA as an impurity adsorbed thereon, is applicable to recovery of an AFE contained in industrial effluents and in products such as a fluorinated polymer aqueous dispersion. Further, it is applicable to recovery of not only an AFE but also a low molecular weight perfluoroalkanoic acid such as trifluoroacetic acid or perfluorobutanoic acid.

This application is a continuation of PCT Application No. PCT/JP2015/059986, filed on Mar. 30, 2015, which is based upon and claims the benefit of priority from Japanese Patent Application No. 2014-072947 filed on Mar. 31, 2014. The contents of those applications are incorporated herein by reference in their entireties.

What is claimed is:

1. A method for recovering an anionic fluorinated emulsifier, which comprises eluting an anionic fluorinated emulsifier from a basic ion exchange resin having a nonionic surfactant physically adsorbed thereon and having the anionic fluorinated emulsifier adsorbed thereon and recovering it as an acid of the anionic fluorinated emulsifier, and which is characterized by comprising a step (1) of bringing the basic ion exchange resin into contact with a water-soluble organic solvent, and then a step (2) of recovering the acid of the anionic fluorinated emulsifier from the basic ion exchange resin from which the ionic surfactant is eluted in the step (1)
wherein the step (2) comprises a step (2-1) of bringing the basic ion exchange resin into contact with an aqueous inorganic acid solution and a water-soluble organic solvent.

2. The method for recovering an anionic fluorinated emulsifier according to claim 1, wherein the step (2) comprises the above step (2-1), and a step (2-2) of separating the mixture into the basic ion exchange resin and a liquid phase and recovering the liquid phase, and a step (2-3) of recovering the acid of the anionic fluorinated emulsifier from the liquid phase, in this order.

3. The method for recovering an anionic fluorinated emulsifier according to claim 1, wherein the step (2-1) comprises a step (2-1-1) of bringing the basic ion exchange resin into contact with the aqueous inorganic acid solution and then a step (2-1-2) of bringing the basic ion exchange resin into contact with the water-soluble organic solution.

4. The method for recovering an anionic fluorinated emulsifier according to claim 3, which comprises the above step (2-1-1), then a step (2-1-1-2) of separating and recovering the basic ion exchange resin, and then the step (2-1-2).

5. The method for recovering an anionic fluorinated emulsifier according to claim 1, wherein the water-soluble organic solvent is at least one member selected from the group consisting of an organic solvent having a nitrile group, an alcohol, a ketone and an ester.

6. The method for recovering an anionic fluorinated emulsifier according to claim 1, wherein the aqueous inorganic acid solution is at least one member selected from the group consisting of an aqueous hydrochloric acid solution, an aqueous sulfuric acid solution, an aqueous nitric acid solution and an aqueous phosphoric acid solution.

7. The method for recovering an anionic fluorinated emulsifier according to claim 1, wherein the water-soluble organic solvent is an organic solvent having a nitrile group, and the organic solvent having a nitrile group is at least one member selected from the group consisting of acetonitrile, propionitrile, butyronitrile and isobutyronitrile.

8. The method for recovering an anionic fluorinated emulsifier according to claim 1, wherein the acid of the anionic fluorinated emulsifier is a fluorinated carboxylic acid.

9. The method for recovering an anionic fluorinated emulsifier according to claim 8, wherein the acid of the anionic fluorinated emulsifier is a $C_{5-7}$ fluorinated carboxylic acid which may have from 1 to 3 etheric oxygen atoms.

10. The method for recovering an anionic fluorinated emulsifier according to claim 1, wherein the basic ion exchange resin is a strongly basic ion exchange resin.

11. The method for recovering an anionic fluorinated emulsifier according to claim 1, wherein the concentration of the aqueous inorganic acid solution is at least 5.0 mass %.

12. The method for recovering an anionic fluorinated emulsifier according to claim 1, wherein the amount of the inorganic acid in the aqueous inorganic acid solution is within such a range that the acid of the anionic fluorinated emulsifier to be eluted/the inorganic acid is from 1/20 to 1.5/1 by the molar ratio.

13. The method for recovering an anionic fluorinated emulsifier according to claim 1, wherein the ratio of the basic ion exchange resin to the aqueous inorganic acid solution is from 90/10 to 10/90 by the mass ratio.

14. The method for recovering an anionic fluorinated emulsifier according to claim 1, wherein the ratio of the basic ion exchange resin to the water-soluble organic solvent is from 10/90 to 70/30 by the mass ratio.

* * * * *

UNITED STATES PATENT AND TRADEMARK OFFICE
CERTIFICATE OF CORRECTION

PATENT NO. : 9,790,163 B2  
APPLICATION NO. : 15/263807  
DATED : October 17, 2017  
INVENTOR(S) : Masahiro Takazawa et al.

Page 1 of 1

It is certified that error appears in the above-identified patent and that said Letters Patent is hereby corrected as shown below:

On the Title Page

Abstract, "the ionic surfactant" should read --the nonionic surfactant--;

In the Specification

Column 2, Line 21, "the ionic surfactant" should read --the nonionic surfactant--; and In the Claims Column 13, Line 12, "the ionic surfactant" should read --the nonionic surfactant--.

Signed and Sealed this  
Sixteenth Day of April, 2019

Andrei Iancu  
*Director of the United States Patent and Trademark Office*